(12) United States Patent
Spacciapoli et al.

(10) Patent No.: US 6,528,488 B2
(45) Date of Patent: Mar. 4, 2003

(54) METHOD FOR TREATING CYSTIC FIBROSIS

(75) Inventors: Peter Spacciapoli, Newbury, MA (US); David M. Rothstein, Lexington, MA (US); Phillip M. Friden, Bedford, MA (US)

(73) Assignee: Demegen, Inc., Pittsburgh, PA (US)

( * ) Notice: Subject to any disclaimer, the term of this patent is extended or adjusted under 35 U.S.C. 154(b) by 0 days.

(21) Appl. No.: 09/226,666

(22) Filed: Jan. 8, 1999

(65) Prior Publication Data

US 2002/0077282 A1 Jun. 20, 2002

(51) Int. Cl.$^7$ .................. A61K 38/08; A61K 38/10; A61K 38/17
(52) U.S. Cl. ............... 514/14; 514/12; 514/13; 514/15; 514/16; 514/21
(58) Field of Search ................ 514/12, 13, 14, 514/15, 16, 17, 18, 19, 21; 530/324, 325, 326, 327, 328, 329, 330, 331

(56) References Cited

U.S. PATENT DOCUMENTS

| | | | | |
|---|---|---|---|---|
| 5,631,228 A | * | 5/1997 | Oppenheim et al. | 514/12 |
| 5,646,119 A | * | 7/1997 | Oppenheim et al. | 514/12 |
| 5,679,665 A | * | 10/1997 | Bergamini et al. | 514/171 |
| 5,885,965 A | * | 3/1999 | Oppenheim et al. | 514/12 |
| 5,912,230 A | * | 6/1999 | Oppenheim et al. | 514/12 |

OTHER PUBLICATIONS

Mendelman et al. Aminoglycoside Penetration, Inactivation, . . . Am. Rev. Respir. Dis. vol. 132, pp. 761–765. 1985.*

Eisenberg et al. A Comparison of Peak Sputum Tobramycin . . . Chest, vol. 111, No. 4, pp. 955–962. Apr. 1997.*

Goldman et al. Human β–Defensin–1 Is a Salt–Sensitive . . . Cell. vol. 88, pp. 553–560. Feb. 21, 1997.*

Anderson et al., "The In Vitro Antimicrobial Properties of the Polypeptide Compound Polymyxin E1 are Equilvalent to Those of Colistin Sulfate" *Pediatric Pulmonolgy Supplement* 17:423 (1998).

Denton and Wilcox, "Antimicrobial Treatment of Pulmonary Colonization and Infection by *Pseudomonas Aeruginosa* in Cystic Fibrosis Patients" *Journal of Antimicrobial Chemotherapy* 40:468–474 (1997).

Hancock, "Peptide Antibiotics" *The Lancet* 349:418/422 (1997).

MacKay et al., "Growth–Inhibitory and Bacterial Effects of Human Parotid Salivary Histidine–Rich Polypeptides on *Streptococcus mutans*" *Infection and Immunity* 44:695–701 (1984).

Nishikata et al., "Salivary Histatin as an Inhibitor of a Protease Produced by the Oral Bacterium Bacteroides Gingivalis" *Biochemical and Biophysical Research Communications* 174:625–630 (1991).

Oppenheim et al., "Histatins, a Novel Family of Histidine–rich Proteins in Human Parotid Secretion" *The Journal of Biological Chemistry* 263:7472–7476 (1988).

Oppenheim et al., "The Primary Structure and Functional Characterization of the Neutral Histidine–rich Polypeptide from Human Parotid Secretion" *The Journal of Biological Chemistry* 261:1177–1182 (1986).

Pollock et al., "Fungistatic and Fungicidal Activity of Human Parotid Salivary Histidine–Rich Polypeptides and *Candida albicans*" *Infection and Immunity* 44:702–707 (1984).

(List continued on next page.)

Primary Examiner—Jeffrey E. Russel
(74) Attorney, Agent, or Firm—Clark & Elbing LLP (57) ABSTRACT

Methods for treating cystic fibrosis in a mammal that include administering to the mammal an effective amount of a histatin, a histatin fragment, or a histatin-related peptide are disclosed.

3 Claims, 5 Drawing Sheets

OTHER PUBLICATIONS

Raj et al., "Salivary Histatin 5: Dependence of Sequence, Chain Length, and Helical Conformation for Candidacidal Activity" The Journal of Biological Chemistry 265:3898–3905 (1990).

Santarpia et al., "A Comparison of the Inhibition of Blastospore Viability and Germ–Tube Development in Candida Albicans by Histidine Peptides and Ketoconazole" *Archs. Oral Biol.* 33:567–573 (1988).

Smith and Ramsey, "Aerosol Administration of Antibiotics" *Respiration* 62:19–24 (1995).

Troxler et al., "Structural Relationship Between Human Salivary Histatins" *J. Dent. Res.* 69:2–6 (1990).

Ramsey, "Management of Pulmonary Disease in Patients with Cystic Fibrosis" Drug Therapy 335:179–188 (1996).

Xu et al., "Primary Structure and Anticandidal Activity of the Major Histatin from Parotid Secretion of the Subhuman Primate, *Macaca fascicularis*" Journal of Dental Research 69:1717–1723 (1990).

* cited by examiner

Histatin 3: Asp-Ser-His-Ala-Lys-Arg-His-His-Gly-Tyr-Lys-Arg-Lys-Phe-His-
           1            5                   10                15
           Glu-Lys-His-His-Ser-His-Arg-Gly-Tyr-Arg-Ser-Asn-Tyr-Leu-Tyr-Asp-Asn
                  20                25              30

Fig. 1

Histatin 5: Asp-Ser-His-Ala-Lys-Arg-His-His-Gly-Tyr-Lys-Arg-Lys-Phe-His-
           1            5                   10                15
           Glu-Lys-His-His-Ser-His-Arg-Gly-Tyr
                  20

METHOD FOR TREATING CYSTIC FIBROSIS

BACKGROUND OF THE INVENTION

The invention relates to methods for treating cystic fibrosis.

Cystic fibrosis is a hereditary disease that affects a number of organs, particularly the lungs and pancreas. The exocrine glands of a cystic fibrosis patient secrete abnormally thick mucous, which blocks the patient's bronchi. As a result, many cystic fibrosis patients have chronic bronchitis; they are also susceptible to pneumonia and other pulmonary infections. In particular, cystic fibrosis patients are susceptible to Pseudomonas infections.

As there is currently no cure for cystic fibrosis, treatments for this disabling disease focus on alleviating the symptoms of the disease. Unfortunately, the infections of many cystic fibrosis patients do not respond to the antibiotics traditionally used to treat pulmonary infections.

SUMMARY OF THE INVENTION

In one aspect, the invention features a method for treating cystic fibrosis in a mammal, such as a human; the method includes administering to the mammal an effective amount of a histatin or a histatin fragment. In preferred methods, the histatin fragment has between 8 and 20 amino acids, inclusive, and more preferably has between 8 and 12 amino acids, inclusive.

For example, the histatin fragment may have the amino acid sequence Ala-Lys-Arg-His-His-Gly-Tyr-Lys-Arg-Lys-Phe-His(SEQ ID NO: 1). Preferably, at least one of the amino acids in this sequence is a D-amino acid. In one preferred method, the fragment has the amino acid sequence D-Ala-D-Lys-D-Arg-D-His-D-His-D-Gly-D-Tyr-D-Lys-D-Arg-D-Lys-D-Phe-D-His.

Figure 2:
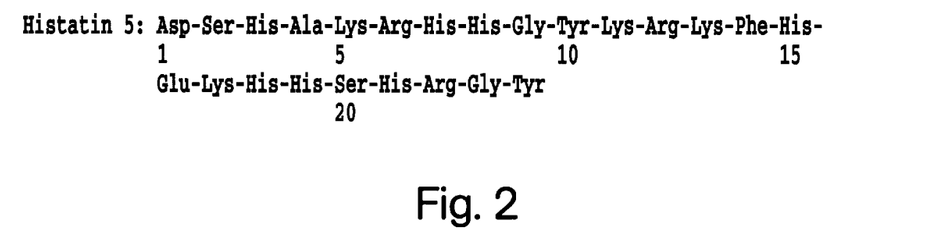
FIG. 2 is the amino acid sequence of histatin 5(SEQ ID NO: 2).

In another preferred method, the histatin is histatin 5 (SEQ ID NO: 2) (shown in FIG. 2); preferably, at least one amino acid of the histatin 5 is a D-amino acid. In yet another preferred method, the histatin or histatin fragment has at least one modification selected from the group consisting of an acyl addition at the N-terminus; a carbamyl addition at the N-terminus; and an amide addition at the C-terminus.

In a second aspect, the invention features a method for treating cystic fibrosis in a mammal, such as a human; the method includes administering to the mammal an effective amount of a histatin-related peptide having between 8 and 20 amino acids, inclusive, where the peptide has the amino acid sequence: R1-R2-R3-R4-R5-R6-R7-R8-R9-R10-R11-R12-R13-R14-R15-R16-R17-R18-R19-R20-R21-R22-R23 (SEQ ID NO: 3), where R1 is Asp or is absent; R2 is Ser or is absent; R3 is His or is absent; R4 is Ala, His, Leu, or is absent; R5 is Lys, Gln, Arg, Orn, or another basic amino acid; R6 is Arg, Gln, Lys, or another basic amino acid; R7 is His, Phe, Tyr, Leu, or another hydrophobic amino acid; R8 is His, Phe, Tyr, Leu, or another hydrophobic amino acid; R9 is Gly, Lys, Arg, Ser, or a basic amino acid; R10 is Tyr; R11 is Lys, His, Phe, Leu, or another hydrophobic amino acid; R12 is Arg, Gln, Lys, or another basic amino acid; R13 is Lys, Gln, Arg, Orn, another basic amino acid, or is absent; R14 is Phe or is absent; R15 is His, Phe, Tyr, Leu, another hydrophobic amino acid, or is absent; R16 is Glu or is absent; R17 is Lys or is absent; R18 is His or is absent; R19 is His or is absent; R20 is Ser or is absent; R21 is His or is absent; R22 is Arg or is absent; and R23 is Gly or is absent.

In preferred methods, at least one of R7, R8, R11, or R15 is Phe. For example, R7 is Phe; R8 is Phe; R11 is Phe; and/or R 15 is Phe. In one preferred method, all of R7, R8, and R15 are Phe. In other preferred methods, R9 is Lys and/or R11 is His. In other preferred methods, at least one of R7, R8, or R15 is Tyr. Preferably, all of R7, R8, and R15 are Tyr.

In another preferred method, at least one of R5 and R13 is Gln; preferably, both R5 and R15 are Gln. In a different preferred method, at least one of R5 and R13 is Orn; preferably, both R5 and R13 are Orn.

In some preferred methods, all of R1, R2, and R3 are absent. In other preferred methods, both R22 and R23 are absent, all of R20, R21, R22, and R23 are absent, or all of R18, R19, R20, R21, R22, and R23 are absent. Examples of preferred peptides include peptides which have the amino acid sequences: Ala- Lys-Arg-Phe-Phe-Gly-Tyr-Lys-Arg-Lys-Phe-Phe (SEQ ID NO: 4) (P-113-F4.5.12); Ala-Lys-Arg- His-His-Lys-Tyr-Lys-Arg-Lys-Phe-His (SEQ ID NO: 5) (P-113-K6); Ala-Lys-Arg-His-His-Gly- Tyr-His-Arg-Lys-Phe-His (SEQ ID NO: 6) (P-113-H8); Ala-Lys-Arg-His-His-Lys-Tyr-His-Arg- Lys-Phe-His (SEQ ID NO: 7) (P-113-K6H8); Ala-Lys-Arg-Tyr-Tyr-Gly-Tyr-Lys-Arg-Lys-Phe-Tyr-NH$_2$ (SEQ ID NO: 8) (P-113-Y4.5.12); Ala-Gln-Arg-His-His-Gly-Tyr-Lys-Arg-Gln-Phe-His- NH$_2$ (SEQ ID NO: 9) (P-113-Q2.10); or Ala- Orn-Arg-Tyr-Tyr-Gly-Tyr-Lys-Arg-Orn-Phe-Tyr-NH$_2$ (SEQ ID NO: 10) (P-113-K2.10O-H4.5.12Y ).

Preferably, the peptide has at least one modification selected from the group consisting of an acyl addition at the N-terminus; a carbamyl addition at the N-terminus; and an amide addition at the C-terminus.

By "hydrophobic amino acid" is meant an amino acid selected from the group consisting of Ala, Val, Leu, Ile, Phe, Trp, Met, and Thr.

By "basic amino acid" is meant an amino acid selected from the group consisting of Lys, Arg, Orn, Gln, and Asn.

The invention provides effective methods for treating cystic fibrosis. According to the invention, histatins, histatin fragments, and histatin-related peptides can be used to combat Pseudomonas infections and other pulmonary infections in cystic fibrosis patients. Histatin derivatives are effective in treating these infections, even in cases where the infections are resistant to traditional antibiotics.

Other features and advantages of the invention will be apparent from the following description and from the claims.

DETAILED DESCRIPTION

Figure 1:
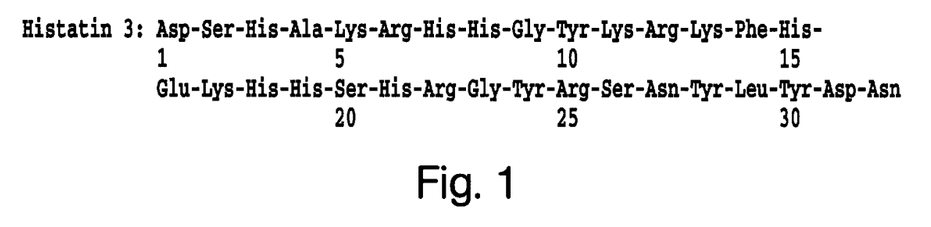
FIG. 1 is the amino acid sequence of histatin 3(SEQ ID NO: 11).

The invention features peptides containing 8 to 20 amino acids; these peptides include defined portions of the amino acid sequence of the naturally occurring protein histatin 3 (SEQ ID NO: 11), which is shown in FIG. 1. In addition, the peptides of the invention include defined portions of the amino acid sequence of histatin 3, with amino acid substitutions at particular positions of the peptides. These peptides are referred to herein as "histatin-related peptides." Histatins (also referred to in the literature as histidine-rich proteins or HRPs) are salivary proteins that are synthesized in the parotid and submandibular-sublingual secretory glands of humans and Old World monkeys and are believed to be part of the extraimmunologic defense system of the oral cavity. The family of naturally occurring human histatins is a group of twelve low molecular weight peptides.

The peptides of the present invention can thus be obtained from naturally occurring sources of histatin; alternatively, they can be obtained by recombinant DNA techniques as expression products from cellular sources. The peptides can also be chemically synthesized.

For example, cloned DNA encoding the histatins or histatin-related peptides may be obtained as described by L. M. Sabatini et al., *Biochem. Biophys. Res. Comm.* 160: 495–502 (1989) and J. C. Vanderspek et al., *Arch. Oral Biol.* 35(2): 137–43 (1990). cDNA encoding the histatin-related peptides can be cloned by recombinant DNA techniques, for instance, by using degenerate oligonucleotides based on the amino acid sequence of histatin-related peptides as primers for polymerase chain reaction amplification.

Alternatively, oligonucleotides encoding histatins or histatin-related peptides can be synthesized chemically using commercially available equipment. They can then be made double-stranded and cloned into vectors for amplification. The histatin-related peptides can be produced in a variety of expression vector/host systems, which are available commercially or can be reproduced according to recombinant DNA and cell culture techniques. The vector/host expression systems can be prokaryotic or eukaryotic, and can include bacterial, yeast, insect, mammalian, and viral expression systems. The construction of expression vectors encoding histatin-related peptides, transfer of the vectors into various host cells, and production of peptides from transformed host cells can be accomplished using genetic engineering techniques, as described in manuals such as J. Sambrook et al., *Molecular Cloning* (2d ed. 1989) and *Current Protocols in Molecular Biology*, (F. M. Ausubel et al., eds.).

The histatin-related peptides encoded by expression vectors may be modified by post-translational processing in a particular expression vector/host cell system. In addition, these peptides can be altered by minor chemical modifications, such as by adding small substituents or by modifying one or more of the covalent bonds within or between the amino acid residues. The substituent groups can be bulky and may include one or more natural or modified amino acids. Useful modifications include the addition of a substituent to either the amino terminus, the carboxyl terminus, or to both termini of the peptide. Particularly useful modifications include acylation or carbamylation of the amino terminus of the peptide, or amidation of the carboxyl terminus of the peptide. These alterations do not significantly diminish the antifungal or antibacterial activities of the peptides and appear to stabilize the peptide in its active form and to aid in the prevention of enzymatic degradation of these peptides.

The peptides can also be made by standard solid phase synthetic methods.

The peptides described herein can be used in preventive treatment as well. The compositions may contain combinations of histatin-related peptides, in order to obtain maximum activity against all developmental forms of fungi or bacteria that cause pulmonary infections. The ionic strength, presence of various mono- and divalent ions, and pH of the compositions may be adjusted to obtain maximum activity of the histatin-related peptides, as described in T. Xu et al., *Infect. Immun.* 59(8): 2549–54 (1991).

Carriers appropriate for administration of pharmaceutical agents to the respiratory system are known and described, for instance, in Pollock et al., U.S. Pat. No. 4,725,576. Compositions for treatment of cystic fibrosis can be administered by various routes; for example, they may be administered by inhalation.

There now follow particular examples that describe the preparation of histatin-related peptides and the antibacterial activity of various histatin-related peptides against strains of *P. aeruginosa*. These examples are provided for the purpose of illustrating the invention, and should not be construed as limiting.

EXAMPLE 1

Isolation of Histatin-related Peptides

The isolation and amino acid sequence determination of human histatins are performed as described in F. G. Oppenheim et al., *J. Biol. Chem.* 263(16): 7472–7477 (1988). Human parotid secretion from healthy adults is stimulated using sour lemon candies, collected with Curby cups in ice-chilled graduated cylinders, pooled, dialyzed and lyophilized. The total protein in the human parotid secretion is subjected to fractionation on Bio-Gel P-2 (Bio-Rad Laboratories, Richmond, Calif.) developed in 0.05 M ammonium formate buffer, pH 4.0. The protein fractionation enriched with histatins is further purified using reverse-phase high-performance liquid chromatography on a $C_{18}$ column. Purified histatins are evaporated to dryness, dissolved in deionized water, quantified by amino acid analysis, lyophilized, and stored at $-20°$ C. until use.

EXAMPLE 2

Chemical Synthesis of Histatin-related Peptides

Histatin-related peptides are synthesized by the solid phase method of B. Merrifield, *Science* 232:341–47 (1986). Peptides are synthesized on a MilliGen/Bioresearch Sam-Two Peptide Synthesizer using Fmoc L-amino acid kits (Millipore, Bedford, Mass.), and purified on a TSK ODS-i2OT $C_{18}$ column (5μm, 4.6×250 nm) using RP-HPLC (Pharmacia-LKB). The purified peptides are quantified by amino acid analysis on a Beckman System 6300 amino acid analyzer.

EXAMPLE 3

Antibacterial Activity of a Histatin-related Peptide Derivative P-113 Against Various Strains of *P. aeruginosa*

Pseudomonas clinical isolates were gathered from cystic fibrosis patients, ranging in age from 14 to 51, from different parts of the country. These isolates were exposed to a variety of antibiotics that are commonly used to treat pulmonary infections, including ceftazidime, imipenem, amikacin, piperacillin, aztreonam, tobramycin, ciprofloxacin, gentamicin, ticarcillin, and timentin. All of the isolates were resistant to the majority of these antibiotics, and some were resistant to all of these antibiotics. Five of these isolates were resistant to all antibiotics tested, including high doses of tobramycin and gentamicin. The susceptibility of these isolates to these antibiotics is summarized in Table 1.

TABLE 1

Background information of cystic fibrosis clinical isolates

| Strain ID | Age | Organism | City | State | Suscepti-bility |
|---|---|---|---|---|---|
| 1-71 AM | 18 | B. cepacia | Toledo | OH | RR |
| 1-76 AM | 51 | P. aeruginosa | Cleveland | OH | R |
| 1-77 AM | 27 | P. aeruginosa | Dallas | TX | R |
| 1-78 AM | 20 | P. aeruginosa | Birmingham | AL | R |
| 1-82 AM | 14 | P. aeruginosa | St. Louis | MO | R |
| 2-17 AM | 10 | P. aeruginosa | Los Angeses | CA | RR |
| 2-24 AM | 15 | P. aeruginosa | Atlanta | GA | R |
| 2-25 AM | 21 | P. aeruginosa | Durham | NC | R |
| 2-87 AM | 21 | P. aeruginosa | Falls Church | VA | R |
| 2-90 AM | 26 | P. aeruginosa | Cincinnati | OH | R |
| 2-98-AL | 33 | P. aeruginosa | Cleveland | OH | RR |
| 3-16 AL | 23 | P. aeruginosa | Providence | RI | R |
| 3-20 AL | 23 | P. aeruginosa | Fort Worth | TX | R |
| 3-36 AM | 26 | P. aeruginosa | Tulsa | OK | R |
| 3-47 AM | 24 | P. aeruginosa | Peoria | IL | R |
| 3-54 AM | 18 | B. cepacia | Lewisburg | PA | RR |
| 3-66 AM | 23 | P. aeruginosa | Oklahoma City | OK | RR |
| 4-34 AL | 19 | P. aeruginosa | Chattanooga | TN | R |
| 4-36 AL | 22 | P. aeruginosa | Oklahoma City | OK | RR |
| 4-68 AL | 17 | P. aeruginosa | Pittsburgh | PA | $r_1$ |
| 4-87 AL | 23 | B. pickettii | Atlanta | GA | $r_2$ |
| 4-97 AL | 17 | P. aeruginosa | San Francisco | CA | R |
| 5-39 AM | 21 | P. aeruginosa | Phoenix | AZ | $r_3$ |

Antibiotics tested against CF isolates: ceftazidime, imipenem, amikacin, piperacillin, aztreonam, tobramycin, ciprofloxacin, gentamicin, ticarcillin, and timentin.
RR = Resistant to all antibiotics, including high doses of tobramycin and gentamicin
R = Resistant to all antibiotics tested
$r_1$ = Resistant to all antibiotics tested except ticarcillin, timentin
$r_2$ = Resistant to all antibiotics tested except piperacillin, ticarcillin, timentin
$r_3$ = Resistant to all antibiotics tested except tobramycin, amikacin These Pseudomonas clinical isolates, as well as a variety of Pseudomonas ATCC strains, were tested for their susceptibility to the histatin derivative having the sequence Ala-Lys-Arg-His-His-Gly-Tyr-Lys-Arg-Lys-Phe- His-NH$_2$ (SEQ ID NO: 1) (P-113). P-113 was used at a concentration of 100 µg/mL to 0.75 µ/mL. P. aeruginosa ATCC 27853 was used as a control in each assay. The ATCC strains were tested using Direct Antibacterial Assay SOP 98-020; the clinical isolates were tested using either the Direct Antibacterial Assay (D) or Alamar Blue Antimicrobial/Antifungal Assay SOP 96-018 (A).

The Direct Assay is an MIC test in microtiter plate format in which cells resuspended in LM broth are exposed to two-fold dilutions of P-113, and the cell density is determined directly after an overnight incubation. Cells are inoculated onto a blood agar plate and incubated for 18 hours at 37° C., and then stored at room temperature for use later in the day. Cells are resuspended and diluted based on the optical density to a final concentration of 5×10$^5$ per ml in LM broth containing two-fold dilutions of antibiotics. After 16–18 hours at 37° C., the optical density is measured with a Molecular Devices Thermonix plate reader. A reading of ~0.3 over background is observed for cells grown in the absence of drug. Readings<0.01 correlated with no visible growth. At least two independent tests were conducted with each strain, and if matching MICs were not obtained, at least one additional test was conducted to determine the MIC.

The composition of LM broth is as follows: 5% Cation-Adjusted Mueller Hinton Broth Supplemented with 2.2 mM Sodium Phosphate, 0.1 mM Magnesium Sulfate, 1.0 mM Sodium Citrate, all to final concentrations. In addition, 0.4 mg ZnCl$_2$, 2.0 mg FeCl$_3$*10H$_2$O, all per liter of medium. Also Glucose, Amino Acid Mix, and Vitamin Mix all from Life Technologies RPMI-1640 Select-Amine Kit, supplemented as instructed by the vendor (Accumed International, Inc., Westlake, Ohio.

The Alamar Blue biological assay was used to compare the effects of various antimicrobial and antifungal agents on Candida albicans with that of a reference standard. The effect of the antimicrobial agent on the growth of C. albicans was monitored using Alamar Blue, a growth indicator dye that is based on the detection of metabolic activity. The dye incorporates an oxidation-reduction (redox) indicator that changes color in response to chemical reduction of growth medium resulting from cell growth. The redox indicator exhibits a colorimetric change in the appropriate oxidation-reduction range relating to cellular metabolic activity and produces a clear, stable and distinct change which can be quantitated using a spectrophotometric microtiter plate reader. A dose response curve was generated using both the test article and the reference standard (positive control). Zero % inhibition was defined as the result obtained when buffer without peptide is added to the cells (negative control). The 50% inhibition points (IC$_{50}$) were used to calculate the activity of the test article, which was expressed as percent activity relative to the reference standard. The IC$_{50}$ for the reference standard fell within the range of 0.60 to 2.24 µg/mL under the conditions of this assay.

The results are shown in Table 2.

TABLE 2

P-113 susceptibility of ATCC strains and clinical cystic fibrosis isolates

| Strain ID[1] | MIC (µg/mL) | Assay** |
|---|---|---|
| ATCC 19142 | 3.1 | D |
| ATCC 19143 | 3.1 | D |
| ATCC 27853 | 6.2 | D |
| ATCC 43393 | 6.25 | D |
| ATCC 51674 | 1.56 | D |
| 332* | 3.1 | D |
| 8050-2* | 3.12 | D |
| 5681-1* | 6.2 | D |
| 1-76 AM | 3.1 | D |
| 1-77 AM | 25 | A |
| 1-78 AM | 1.6 | A |
| 1-82 AM | 1.56 | D |
| 2-17 AM | 3.12 | D |
| 2-24 AM | 1.6 | A |
| 2-25 AM | 1.56 | D |
| 2-87 AM | 1.56 | D |
| 2-90 AM | 1.56 | D |
| 2-98-AL | >100 | D |
| 3-16 AL | 1.6 | A |
| 3-20 AL | 3.12 | D |
| 3-36 AM | 3.12 | D |
| 3-47 AM | 1.6 | A |
| 3-66 AM | 3.12 | D |
| 4-34 AL | 3.1 | A |
| 4-36 AM | 1.6 | A |
| 4-68 AL | 4.1 | A |
| 4-97 AL | 3.12 | D |
| 5-39 AM | 6.25 | D |
| 2192* | 6.25 | D |

[1]Strains from ATCC are designated. Most of the other strains are clinical CF isolates obtained from Dr. Lisa Saiman at Columbia University. Four strains (indicated with an asterisk) were obtained from Dr. Gerry Pier at Harvard University As shown in Table 2, the peptide P-113 was effective against nearly all of the Pseudomonas strains tested.

EXAMPLE 4

Antibacterial Activity of a First Group of Histatin-related Peptides Against P. aeruginosa Histatin derivatives having the following amino acid sequences were tested for activity against P. aeruginosa:
Ala-Lys-Arg-His-His-Gly-Tyr-Lys-Arg-Lys-Phe-His-NH$_2$ (SEQ ID NO: 1) (P-113); Ala-Lys-Arg- His-His-Lys-Tyr-Lys-Arg-Lys-Phe-His-NH$_2$ (SEQ ID NO: 5) (P-113-K6); Ala-Lys-Arg-His-His- Gly-Tyr-His-Arg-Phe-His-NH$_2$ (SEQ ID NO: 6) (P-113-H8); Ala-Lys-Arg-His-His-Gly-Tyr- His-Arg-Lys-Phe-His-NH$_2$ (SEQ ID NO: 7) (P-113-K6H8); Ac-Ala-Lys-Arg-His-His-Gly-Tyr-Lys- Arg-Lys-Phe-His-NH$_2$ (SEQ ID NO: 1) (P-113-NA); and Ala-Lys-Arg-Phe-Phe-Gly-Tyr-Lys-Arg- Lys-Phe-Phe NH$_2$ (SEQ ID NO: 4) (P113-F4.5.12).

The standard procedure used for testing activity was incubation of the bacterial strain with the peptide for one hour at 37° C., followed by plating at two dilutions.

Figure 3:
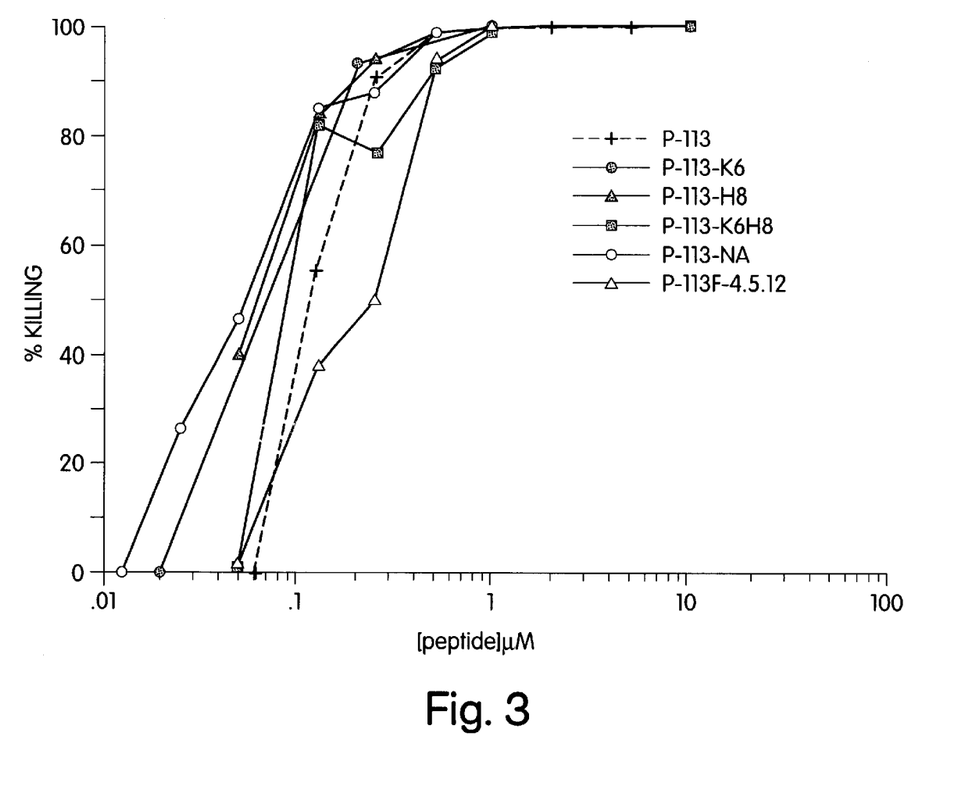
FIGS. 3, 4, 5, and 6 are graphs showing the percentages of cells in *P. aeruginosa* assays killed by peptides of the invention.

The results are shown in FIG. 3. As shown there, the peptides all showed antimicrobial activity against P. aeruginosa. All of the peptides were capable of killing at least 80% of the bacteria at peptide concentrations of about 0.5 μM and higher.

EXAMPLE 5

Antibacterial Activity of a Second Group of Histatin-related Peptides Against P. aeruginosa Peptides having the following amino acid sequences (including P-113, as in Example 4) were tested for activity against P. aeruginosa under the conditions described above:
Ala-Lys-Arg-His-His-Gly-Tyr-Lys-Arg-Lys-Phe-His-NH$_2$ (SEQ ID NO: 1) (P-113); Ala-Lys-Arg- Tyr-Tyr-Gly-Tyr-Lys-Arg-Lys-Phe-Tyr-NH$_2$ (SEQ ID NO: 8) (P-113-Y4.5.12); Ala-Lys-Arg-Leu- Leu-Gly-Tyr-Lys-Arg-Lys-Phe-Leu-NH$_2$ (SEQ ID NO: 12) (P-113-L4.5.12); Ala-Gln-Arg-His-His- Gly-Tyr-Lys-Arg-Gln-Phe-His-NH$_2$ (SEQ ID NO: 9) (P-113-Q2.10); Ala-Lys-Gln-His-His-Gly- Tyr-Lys-Gln-Lys-Phe-His-NH$_2$ (SEQ ID NO: 13) (P-113-Q3.9); and Ala-Gln-Gln-His-His-Gly-Tyr- Lys-Gln-Gln-Phe-His-NH$_2$ (SEQ ID NO: 14) (P-113-Q2.3.9.10).

Figure 4:
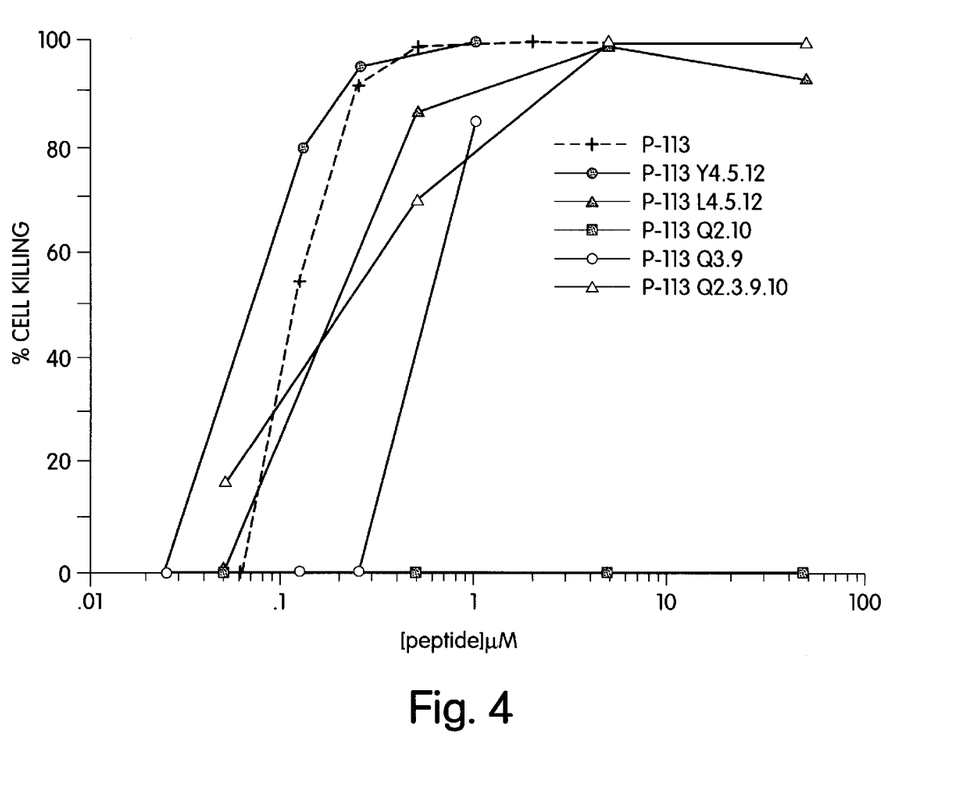

The results are shown in FIG. 4. As shown there, P-113, P-113 Y4.5.12, and P-113 Q2.10 were very active against P. aeruginosa; P-113 Q3.9 and P-113 L4.5.12 were also active. P-113 Q2.3.9.10 was inactive against P. aeruginosa, even at high peptide concentrations.

EXAMPLE 6

Antibacterial Activity of a Third Group of Histatin-related Peptides Against P. aeruginosa Peptides having the following amino acid sequences were tested for antibacterial activity against P. aeruginosa:
Ala-Lys-Arg-Leu-Leu-Ser-Tyr-Lys-Arg-Lys-Phe-Leu-NH$_2$ (SEQ ID NO: 15) (P-113-G6S- H4.5.12L); Ala-Orn-Arg-Tyr-Tyr-Gly-Tyr-Lys-Arg-Orn-Phe-Tyr-NH$_2$ (SEQ ID NO: 10)(P-113- K2.10O-H4.5.12Y); Ala-Lys-Lys-His-His-Gly-Tyr-Lys-Lys-Lys-Phe-His-NH$_2$ (SEQ ID NO: 16) (P113-R3.9K); His-Lys-Lys-His-His-Lys-Tyr-His-Lys-Lys-Phe-His-NH$_2$ (SEQ ID NO: 17) (P-113 H-amphipathic); Leu-Lys-Lys-Phe-Phe-Gly-Tyr-Leu-Lys-Lys-Phe-Phe-NH$_2$ (SEQ ID NO: 18) (P- 113 amphipathic); and Ala-Gln-Gln-His-His-Gly-Tyr-Lys-Gln-Gln-Phe-His-NH$_2$ (SEQ ID NO: 14) (P-113-KR2.3.9.10Q).

Figure 5:
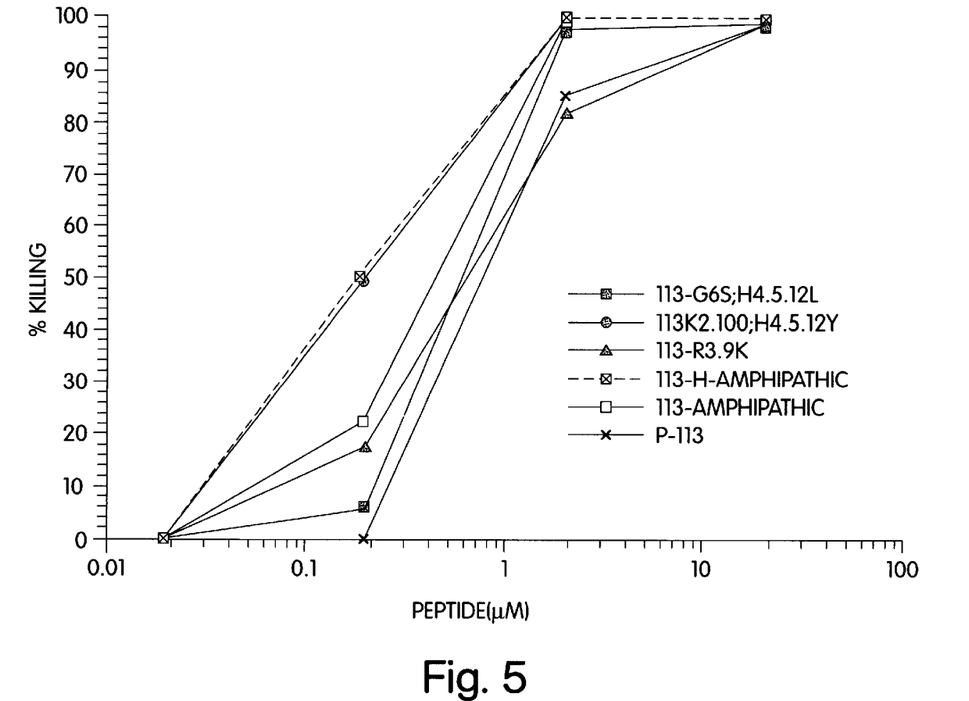
Figure 6:
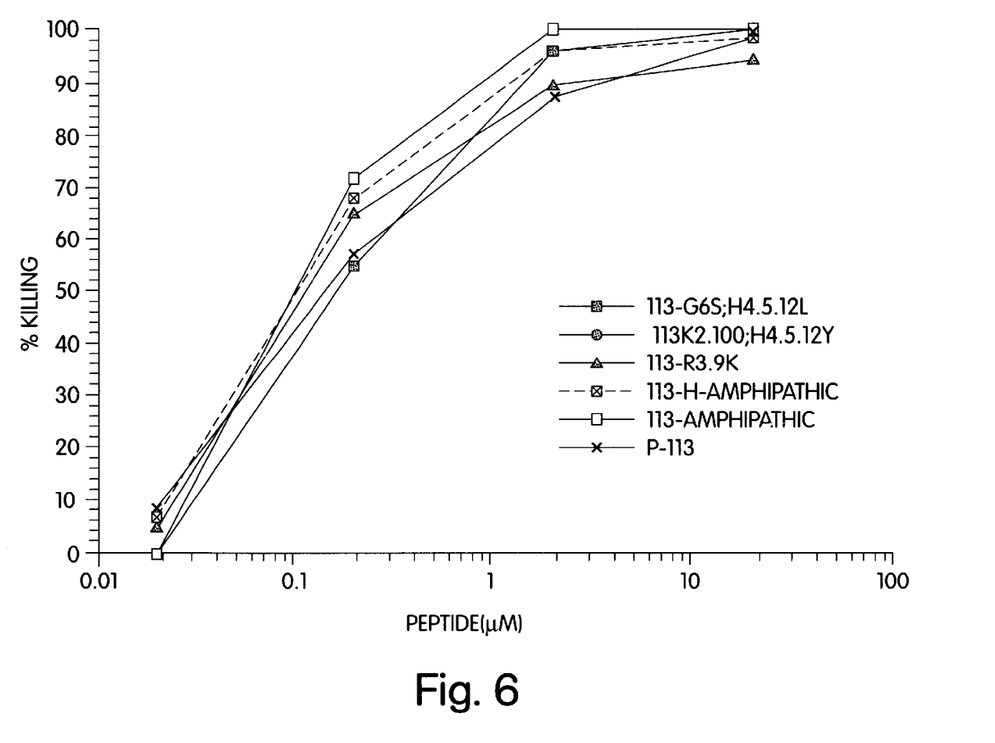

The results for two runs of the same assay are shown in FIGS. 5 and 6. As shown there, all of the peptides tested in this series had activity against P. aeruginosa. All of the peptides killed at least 80% of the cells at peptide concentrations of about 2 μM.

EXAMPLE 6

Antibacterial Activity of Histatin-5 and P-113 Against P. aeruginosa

P-113 and His-5 were tested against P. aeruginosa under the conditions described in the preceding examples. The dilution values were as follows: expected-2000 cfu/plate (in broth) from dilution A. A=1/2.5×dilution; plate 50 μl. B=1/2.5×dilution; plate 25 μl.

The results are shown in Table 3. Both peptides were effective in killing these bacteria, with P-113 exhibiting greater efficacy than His-5.

TABLE 3

| P-113 and His 5: Killing of P. aeruginosa | | | | | |
|---|---|---|---|---|---|
| | | cfu/plate | | | % killing |
| Control 1 | A | 168 | 179 | 165 | |
| | B | 76 | 85 | 97 | |
| Control 2 | A | 234 | 217 | 248 | |
| | B | 124 | 152 | 130 | |
| His-5 200 μM | A | 0 | 0 | | 100 |
| | B | 0 | 0 | | 100 |
| P-113 200 μM | A | 0 | 0 | | 100 |
| | B | 0 | 0 | | 100 |
| His-5 50 μM | A | 0 | 1 | | 99 |
| | B | 0 | 2 | | 98 |
| P-113 50 μM | A | 0 | 0 | | 100 |
| | B | 0 | 1 | | 99 |
| His-5 5 μM | A | 143 | 159 | | 24 |
| | B | 73 | 68 | | 36 |
| P-113 5 μM | A | 1 | 4 | | 99 |
| | B | 0 | 4 | | 98 |
| His-5 0.5 μM | A | 150 | 164 | | 19 |
| | B | 90 | 96 | | 16 |
| P-113 5 μM | A | 133 | 170 | | 24 |
| | B | 88 | 85 | | 22 |

All publications and patents mentioned in this specification are herein incorporated by reference to the same extent as if each individual publication or patent was specifically and individually indicated to be incorporated by reference.

Other Embodiments

From the foregoing description, it will be apparent that variations and modifications may be made to the invention described herein to adopt it to various usages and conditions. Such embodiments are also within the scope of the following claims.

SEQUENCE LISTING

<160> NUMBER OF SEQ ID NOS: 18

<210> SEQ ID NO 1
<211> LENGTH: 12
<212> TYPE: PRT
<213> ORGANISM: Artificial Sequence
<220> FEATURE:
<223> OTHER INFORMATION: Internal fragment

<400> SEQUENCE: 1

Ala Lys Arg His His Gly Tyr Lys Arg Lys Phe His
 1               5                  10

<210> SEQ ID NO 2
<211> LENGTH: 24
<212> TYPE: PRT
<213> ORGANISM: Homo sapiens

<400> SEQUENCE: 2

Asp Ser His Ala Lys Arg His His Gly Tyr Lys Arg Lys Phe His Glu
 1               5                  10                  15

Lys His His Ser His Arg Gly Tyr
            20

<210> SEQ ID NO 3
<211> LENGTH: 23
<212> TYPE: PRT
<213> ORGANISM: Artificial Sequence
<220> FEATURE:
<223> OTHER INFORMATION: Derived from Homo sapiens
<220> FEATURE:
<221> NAME/KEY: VARIANT
<222> LOCATION: (1)...(1)
<223> OTHER INFORMATION: Asp or absent.
<220> FEATURE:
<221> NAME/KEY: VARIANT
<222> LOCATION: (2)...(2)
<223> OTHER INFORMATION: Ser or absent.
<220> FEATURE:
<221> NAME/KEY: VARIANT
<222> LOCATION: (3)...(3)
<223> OTHER INFORMATION: His or absent.
<220> FEATURE:
<221> NAME/KEY: VARIANT
<222> LOCATION: (4)...(4)
<223> OTHER INFORMATION: Ala, His, Leu or absent.
<220> FEATURE:
<221> NAME/KEY: VARIANT
<222> LOCATION: (5)...(5)
<223> OTHER INFORMATION: Lys, Gln, Arg, Orn, or another basic amino acid
<220> FEATURE:
<221> NAME/KEY: VARIANT
<222> LOCATION: (6)...(6)
<223> OTHER INFORMATION: Arg, Gln, Lys, or another basic amino acid
<220> FEATURE:
<221> NAME/KEY: VARIANT
<222> LOCATION: (7)...(7)
<223> OTHER INFORMATION: His, Phe, Tyr, Leu, or another hydrophobic
      amino acid
<220> FEATURE:
<221> NAME/KEY: VARIANT
<222> LOCATION: (8)...(8)
<223> OTHER INFORMATION: His, Phe, Tyr, Leu, or another hydrophobic
      amino acid
<220> FEATURE:
<221> NAME/KEY: VARIANT
<222> LOCATION: (9)...(9)
<223> OTHER INFORMATION: Gly, Lys, Arg, Ser, or a basic amino acid
<220> FEATURE:
<221> NAME/KEY: VARIANT
<222> LOCATION: (10)...(10)

```
<223> OTHER INFORMATION: Tyr
<220> FEATURE:
<221> NAME/KEY: VARIANT
<222> LOCATION: (11)...(11)
<223> OTHER INFORMATION: Lys, His, Phe, Leu, or another hydrophobic
      amino acid
<220> FEATURE:
<221> NAME/KEY: VARIANT
<222> LOCATION: (12)...(12)
<223> OTHER INFORMATION: Arg, Gln, Lys, or another basic amino acid
<220> FEATURE:
<221> NAME/KEY: VARIANT
<222> LOCATION: (13)...(13)
<223> OTHER INFORMATION: Lys, Gln, Arg, Orn, another basic amino acid,
      or is absent
<220> FEATURE:
<221> NAME/KEY: VARIANT
<222> LOCATION: (14)...(14)
<223> OTHER INFORMATION: Phe or is absent
<220> FEATURE:
<221> NAME/KEY: VARIANT
<222> LOCATION: (15)...(15)
<223> OTHER INFORMATION: His, Phe, Tyr, Leu, another hydrophobic amino
      acid, or is absent
<220> FEATURE:
<221> NAME/KEY: VARIANT
<222> LOCATION: (16)...(16)
<223> OTHER INFORMATION: Glu or is absent
<220> FEATURE:
<221> NAME/KEY: VARIANT
<222> LOCATION: (17)...(23)
<223> OTHER INFORMATION: 17 is Lys or is absent; 18 is His or is absent;
      19 is His or is absent; 20 is Ser or is absent; 21 is His or is
      absent; 22 is Arg or is absent; 23 is Gly or is absent.

<400> SEQUENCE: 3

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 4
<211> LENGTH: 12
<212> TYPE: PRT
<213> ORGANISM: Artificial Sequence
<220> FEATURE:
<223> OTHER INFORMATION: Derived from Homo sapiens

<400> SEQUENCE: 4

Ala Lys Arg Phe Phe Gly Tyr Lys Arg Lys Phe Phe
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Derived from Homo sapiens

<400> SEQUENCE: 5

Ala Lys Arg His His Lys Tyr Lys Arg Lys Phe His
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Derived from Homo sapiens

<400> SEQUENCE: 6
```

```
-continued

Ala Lys Arg His His Gly Tyr His Arg Lys Phe His
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: Derived from Homo sapiens

<400> SEQUENCE: 7

Ala Lys Arg His His Lys Tyr His Arg Lys Phe His
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Derived from Homo sapiens

<400> SEQUENCE: 8

Ala Lys Arg Tyr Tyr Gly Tyr Lys Arg Lys Phe Tyr
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: Derived from Homo sapiens

<400> SEQUENCE: 9

Ala Gln Arg His His Gly Tyr Lys Arg Gln Phe His
 1               5                  10

<210> SEQ ID NO 10
<211> LENGTH: 12
<212> TYPE: PRT
<213> ORGANISM: Artificial Sequence
<220> FEATURE:
<223> OTHER INFORMATION: Derived from Homo sapiens
<220> FEATURE:
<221> NAME/KEY: VARIANT
<222> LOCATION: (2)...(2)
<223> OTHER INFORMATION: Xaa is Ornithine
<220> FEATURE:
<221> NAME/KEY: VARIANT
<222> LOCATION: (10)...(10)
<223> OTHER INFORMATION: Xaa is Ornithine

<400> SEQUENCE: 10

Ala Xaa Arg Tyr Tyr Gly Tyr Lys Arg Xaa Phe Tyr
 1               5                  10

<210> SEQ ID NO 11
<211> LENGTH: 32
<212> TYPE: PRT
<213> ORGANISM: Homo sapien

<400> SEQUENCE: 11

Asp Ser His Ala Lys Arg His His Gly Tyr Lys Arg Lys Phe His Glu
 1               5                  10                  15

Lys His His Ser His Arg Gly Tyr Arg Ser Asn Tyr Leu Tyr Asp Asn
                20                  25                  30

<210> SEQ ID NO 12
```

```
<211> LENGTH: 12
<212> TYPE: PRT
<213> ORGANISM: Artificial Sequence
<220> FEATURE:
<223> OTHER INFORMATION: Derived from Homo sapiens

<400> SEQUENCE: 12

Ala Lys Arg Leu Leu Gly Tyr Lys Arg Lys Phe Leu
 1               5                  10

<210> SEQ ID NO 13
<211> LENGTH: 12
<212> TYPE: PRT
<213> ORGANISM: Artificial Sequence
<220> FEATURE:
<223> OTHER INFORMATION: Derived from Homo sapiens

<400> SEQUENCE: 13

Ala Lys Gln His His Gly Tyr Lys Gln Lys Phe His
 1               5                  10

<210> SEQ ID NO 14
<211> LENGTH: 12
<212> TYPE: PRT
<213> ORGANISM: Artificial Sequence
<220> FEATURE:
<223> OTHER INFORMATION: Derived from Homo sapiens

<400> SEQUENCE: 14

Ala Gln Gln His His Gly Tyr Lys Gln Gln Phe His
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Derived from Homo sapiens

<400> SEQUENCE: 15

Ala Lys Arg Leu Leu Ser Tyr Lys Arg Lys Phe Leu
 1               5                  10

<210> SEQ ID NO 16
<211> LENGTH: 12
<212> TYPE: PRT
<213> ORGANISM: Artificial Sequence
<220> FEATURE:
<223> OTHER INFORMATION: Derived from Homo sapiens

<400> SEQUENCE: 16

Ala Lys Lys His His Gly Tyr Lys Lys Lys Phe His
 1               5                  10

<210> SEQ ID NO 17
<211> LENGTH: 12
<212> TYPE: PRT
<213> ORGANISM: Artificial Sequence
<220> FEATURE:
<223> OTHER INFORMATION: Derived from Homo sapiens

<400> SEQUENCE: 17

His Lys Lys His His Lys Tyr His Lys Lys Phe His
 1               5                  10

<210> SEQ ID NO 18
<211> LENGTH: 12
```

```
<212> TYPE: PRT
<213> ORGANISM: Artificial Sequence
<220> FEATURE:
<223> OTHER INFORMATION: Derived from Homo sapiens

<400> SEQUENCE: 18

Leu Lys Lys Phe Phe Gly Tyr Leu Lys Lys Phe Phe
 1               5                  10
```

What is claimed is:

1. A method for treating cystic fibrosis in a mammal comprising administering to said mammal, by inhalation, an effective amount of a polypetide having the amino acid sequence D-Ala-D-Lys-D-Arg-D-His-D-His-D-Gly-D-Tyr-D-Lys-D-Arg-D-Lys-D-Phe-D-His (SEQ ID NO: 1).

2. The method of claim 1, wherein said mammal is a human.

3. The method of claim 1, wherein said peptide has at least one modification selected from the group consisting of (a) an acyl addition at the N-terminus;

(b) a carbamyl addition at the N-terminus; and (c) an amide addition at the C-terminus.

* * * * *